(12) United States Patent
Litke et al.

(10) Patent No.: US 7,660,427 B2
(45) Date of Patent: Feb. 9, 2010

(54) DEFORMABLE SOFT MOLDING COMPOSITIONS

(75) Inventors: Alan Edward Litke, Waterbury, CT (US); JoAnn DeMarco, Wethersfield, CT (US); Victor Karol Kadziela, New Britain, CT (US)

(73) Assignee: Henkel Corporation, Rocky Hill, CT (US)

( * ) Notice: Subject to any disclaimer, the term of this patent is extended or adjusted under 35 U.S.C. 154(b) by 0 days.

(21) Appl. No.: 12/353,705

(22) Filed: Jan. 14, 2009

(65) Prior Publication Data

US 2009/0124783 A1    May 14, 2009

Related U.S. Application Data

(60) Division of application No. 10/922,458, filed on Aug. 20, 2004, now Pat. No. 7,495,034, which is a continuation-in-part of application No. 10/081,564, filed on Feb. 22, 2002, now Pat. No. 6,829,362.

(60) Provisional application No. 60/585,149, filed on Jul. 2, 2004.

(51) Int. Cl.
C08F 2/50 (2006.01)
H04R 25/02 (2006.01)
H04R 25/00 (2006.01)
C08J 3/28 (2006.01)

(52) U.S. Cl. .............. 381/322; 381/328; 381/312; 522/90; 522/96; 522/150; 522/152; 522/153; 522/173; 522/174; 522/178; 522/182; 264/494; 264/496

(58) Field of Classification Search .......... 522/90, 522/96, 150, 152, 153, 173, 174, 178, 182; 381/312, 328, 322; 181/129, 130, 135; 29/896.21; 364/474.05, 468, 474.24; 264/22, 494, 496
See application file for complete search history.

(56) References Cited

U.S. PATENT DOCUMENTS

| | | | |
|---|---|---|---|
| 3,527,901 A | 9/1970 | Geib | |
| 4,375,016 A | 2/1983 | Harada | |
| 4,439,600 A | 3/1984 | Moran, Jr. | |
| 4,870,688 A | 9/1989 | Voroba et al. | |
| 4,900,763 A | 2/1990 | Kraushaar | |
| 4,932,750 A | 6/1990 | Ansel et al. | |
| 4,973,611 A | 11/1990 | Puder | |
| 5,002,151 A | 3/1991 | Oliveira et al. | |
| 5,021,467 A | 6/1991 | Yokoshima et al. | |
| 5,036,113 A | 7/1991 | Boon et al. | |
| 5,185,234 A | 2/1993 | Nakatsukasa et al. | |
| 5,201,007 A | 4/1993 | Ward et al. | |
| 5,401,806 A | 3/1995 | Braden et al. | |
| 5,487,012 A * | 1/1996 | Topholm et al. | ............ 700/163 |
| 5,536,758 A | 7/1996 | Boldt | |
| 5,554,712 A | 9/1996 | Huynh-Tran et al. | |
| 5,679,721 A | 10/1997 | Courtoy et al. | |
| 5,763,503 A | 6/1998 | Cowperthwaite et al. | |
| 5,847,021 A | 12/1998 | Tortorello et al. | |
| 5,916,669 A | 6/1999 | Parker et al. | |
| 6,022,311 A | 2/2000 | Juneau et al. | |
| 6,048,911 A | 4/2000 | Shustack et al. | |
| 6,107,361 A | 8/2000 | Tortorello et al. | |
| 6,110,593 A | 8/2000 | Szum et al. | |
| 6,136,497 A | 10/2000 | Melisaris et al. | |
| 6,205,227 B1 | 3/2001 | Mahoney et al. | |
| 6,387,976 B1 | 5/2002 | Flat | |
| 6,413,697 B1 | 7/2002 | Melisaris et al. | |
| 6,503,960 B1 * | 1/2003 | Kadziela et al. | ............... 522/78 |
| 6,533,062 B1 | 3/2003 | Widmer et al. | |
| 6,540,045 B1 | 4/2003 | Widmer et al. | |
| 6,829,362 B1 | 12/2004 | Kadziela et al. | |
| 7,514,477 B2 * | 4/2009 | Klare et al. | ................... 522/81 |

FOREIGN PATENT DOCUMENTS

| | | |
|---|---|---|
| EP | 0780712 A2 | 6/1997 |
| EP | 0849296 A2 | 6/1998 |
| GB | 2338238 A | 12/1999 |
| WO | WO 01/27181 A1 | 4/2001 |

* cited by examiner

*Primary Examiner*—Sanza L McClendon
(74) *Attorney, Agent, or Firm*—Steven C. Bauman

(57) ABSTRACT

A curable composition and method for producing a tear resistant, yet soft and deformable in-the-ear product yielding the user greater comfort and durability. The curable composition incorporated into a hearing aid apparatus provides a deformable, yet tear resistant housing, which may be mated to a soft tip component. The hearing aid housing provides better comfort, durability and acoustic performance for a variety of ear canal shapes. The curable composition that provides these properties includes at least one urethane acrylate oligomer, at least one reactive diluent and a cure system. The composition when cured desirably produces a tear strength of at least about 75 pli and a hardness of about Shore A 60 to about 75.

7 Claims, 1 Drawing Sheet

DEFORMABLE SOFT MOLDING COMPOSITIONS

RELATED U.S. APPLICATION DATA

This application is a division of U.S. patent application Ser. No. 10/922,458, filed Aug. 20, 2004, which is a continuation-in-part of U.S. patent application Ser. No. 10/081,564, filed Feb. 22, 2002, now U.S. Pat. No. 6,829,362 and further claims benefit to U.S. Provisional Application No. 60/585,149, filed Jul. 2, 2004, which are incorporated by reference herein.

BACKGROUND OF THE INVENTION

1. Field of the Invention

The present invention relates to curable compositions and methods for producing tear resistant, yet soft and deformable in-the-ear products yielding the user greater comfort and durability. Additionally, the nature of the inventive soft body design provides better acoustic performance for a variety of ear canal shapes and various motion affecting the ear canal, such as head and jaw movements.

2. Brief Description of Related Technology

Hearing aids need to be durable, comfortable and reliable. Otherwise, end users may oftentimes resist their use. Durability focuses on the integrity of the material, long lasting, and integrity of the bonding of the components. Comfortability implies that the device is soft when placed in the ear canal. Reliability implies superior acoustic quality throughout the life of the device, which requires adequate sealing within the ear canal. The challenges to satisfy the comfort and reliability objectives are due to the dynamic nature of the ear canal, and the geometric alterations of the ear canal due to natural anatomical movement. The dynamic nature of the ear canal varies from person to person, and even the anatomical shape varies from ear to ear of the same person. The canal shape is geometrically altered by motion from the head and the mandible, usually causing elliptical elongation. These differences in canal shape and changes due to body movement make it difficult to achieve a comfortable and true acoustic seal.

Challenges in meeting comfort as well as durability are due to the nature of the ear canal and materials able to use. In the past, hearing aids were made from hard acrylic materials which have proven to be durable but uncomfortable. And when the device was displaced by motion, a leakage of sound pressure occurred. Attempts were made to use rubber instead of the hard acrylic materials, such as in U.S. Pat. No. 3,527,901 to Geib. Rubber is softer and more resilient than hard acrylic but it is not very comfortable and still lacks a true acoustic seal upon motion.

Attempt to use soft vinyl materials have also not been entirely successful in meeting the aforementioned characteristics. Although vinyl may be softer than rubber and offers a better acoustic seal, soft vinyl lacks durability, and in fact, after a relatively short period of time it shrinks, turns yellow and becomes hard or brittle. It is recommended in the hearing aid industry to replace vinyl components for behind-the-ear ear molds at least annually.

Silicone materials have also been used as the housing material, such as disclosed in U.S. Pat. No. 6,022,311 to Juneau et al. The '311 patent discloses a two layer silicone housing bonded with an adhesive to the plastic faceplate of the device. Although silicone has a longer wear life than vinyl materials, it lacks strong bonding properties to the plastics commonly used in heating aid instrumentality.

Polyurethanes have in the past been used for hearing aid components. For example, U.S. Pat. No. 5,763,503 to Cowperthwaite et al. discloses a housing for an in-the-ear hearing aid made from a solid and stiff polyurethane, polyesters or polyether to support the instrumentality. The Shore D hardness is from 50 to 90. Polyurethane has been proven to provide a better acoustic seal than polyvinyl. The properties needed for the housing require a stiff, firm, harder material to support the instrumentality which conflict with the objective for softer, comfortable fit within the ear canal.

Thus, instead of focusing on the housing material, attempts have been made to supply an attachment to the housing such as a covering or sleeve. This preserves the durability of the original housing material, while adding a comfort factor. For instance, U.S. Pat. No. 4,870,688 to Voroba et al. discloses a soft, resilient covering which is affixed to the rigid bonding of the ear shell. No covering material or details on affixing the covering to the ear shell were disclosed. Another example, U.S. Pat. No. 5,002,151 to Oliveira et al., discloses a disposable sleeve made of a soft polyurethane retarded recovery foam attached to the ear piece by mating of screw threads on the sleeve and the ear piece. Unfortunately, a sleeve concept would lack durability and require continual replacement. The sleeve creates a safety concern due to the possibility of this attachment to slip off from motion in the ear canal and possibly lodging in the ear canal. The inadequacy and quality of the disposable sleeves bonded to the housing is a major concern.

Therefore, there is a need for a deformable, soft hearing aid housing, which is tear resistant, and thus, a durable, long-lasting material. It is desired that such hearing aid housing be comfortable, soft enough, and reliable to provide superior acoustics.

SUMMARY OF THE INVENTION

In one aspect of the present invention, there is provided a curable composition, which includes (a) at least one urethane acrylate oligomer; (b) at least one reactive diluent; and (c) a cure system, where the composition when cured produces one or more properties selected from tear strength of at least about 75 pli, Shore A hardness of about 60 to about 75, and tensile modulus of at least about 2,150 psi.

In another aspect of the present invention, there is provided a curable composition, which includes (a) at least one urethane acrylate oligomer; (b) at least one reactive diluent; and (c) a cure system, where the composition when cured produces two or more properties selected from tear strength of at least about 75 pli, Shore A hardness of about 60 to about 75, and tensile modulus of at least about 2,150 psi.

In yet another aspect of the present invention, there is provided a curable composition, which includes an aliphatic polyester urethane diacrylate present in amounts of about 30% to about 45% by weight, isobornyl acrylate present in amounts of about 40% to about 50% by weight, 2(2-ethoxyethoxy) ethyl acrylate present in amounts of about 5% to about 25% by weight, and a photoinitiator present in amounts of about 0.5% to about 10% by weight of the composition.

In still another aspect of the present invention, there is provided a hearing aid housing, which includes the reaction product of at least one urethane acrylate oligomer and at least one reactive diluent. The composition when cured produces a tear strength of at least about 75 pli.

In still yet another aspect of the present invention, there is provided a method of making a hearing aid housing, which includes the steps of: combining a curable composition, which includes at least one urethane acrylate oligomer, at least one reactive diluent and a cure system; pouring the curable composition into a mold cavity of a mold; and exposing the composition to photo-radiation for a time and intensity sufficient to fully cure the composition to produce a tear strength of at least about 75 pli.

In an additional aspect of the present invention, there is provided a method of making a hearing aid housing, which includes the steps of: providing data of the three-dimensional shape of an area in an individual's ear for application of a hearing aid housing; combining a curable composition, which includes at least one urethane acrylate oligomer, at least one reactive diluent and a cure system; exposing the composition to photo-radiation for a time and intensity sufficient to cure a layer on the surface of the composition which corresponds to a cross-section of the three-dimensional area in the individual's ear; covering the cured layer with a new layer of the composition and exposing the new layer to photo-radiation for a time and intensity sufficient to cure the new layer; and repeating step (c) until the hearing aid housing is formed.

DETAILED DESCRIPTION OF THE INVENTION

Figure 1:
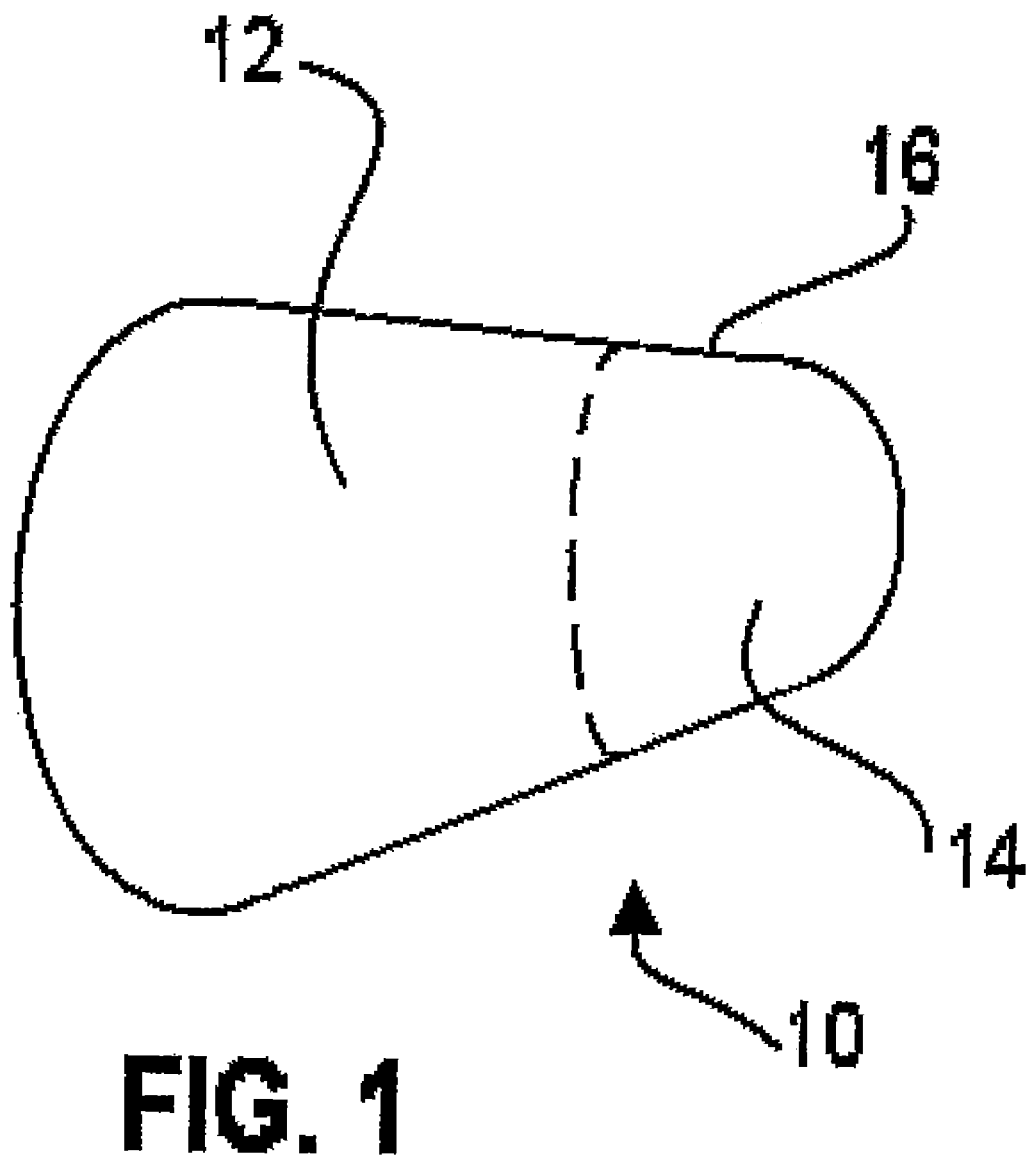
FIG. 1 shows a perspective view of a hearing aid housing attached to a soft tip in accordance with an embodiment of the present invention.

As shown in FIG. 1, a hearing aid housing 12 (also commonly referred to as a shell) of hearing aid assembly 10 is constructed to fit within the outer ear of the wearer. Adhesively mated to the housing 12 is a soft tip 14 which projects through the concha and into the auditory canal area. The outer wall 16 of soft tip 14 forms a seal at the opening and in the auditory canal.

The hearing aid housing 12 typically contains amplifier means, volume adjustment control and battery access door, all of which are not shown. In operation, the amplifier means for receiving and amplifying unamplified sound is connected to a sound tube adapted for conveying sound from the amplifier means to the end of the tube inside the ear canal. The soft tip 14 encloses the tube for conveying sound and may contain other ports for various uses such as vent apertures. The end of the sound tube is positioned to deliver sound energy generally along the axis of the ear canal when inserted.

To provide a comfortable fit and an acoustic seal in the wearer's ear, hearing aid housing 12 is formed of a curable composition, which is highly tear resistant yet deformable to provide an acoustic seal and be comfortable to the user. The sealing and comfort properties are important for commercial viability. Additionally, a soft tip 14 may be mated to the hearing aid housing 12. The soft tip 14 may be formed of the same curable composition as the hearing aid housing, disclosed herein, or alternatively the curable compositions disclosed in Applicants' U.S. patent application Ser. No. 10/081,564, entitled "Soft Molding Compound" and filed on Feb. 22, 2002, of which the present application is a continuation-in-part, and which is incorporated herein by reference in its entirety.

The inventive hearing aid components of the present invention are durable to provide long-lasting quality. The curable composition that forms the hearing aid housing includes the reaction product of at least one urethane acrylate oligomer and at least one reactive diluent, designed to provide a tear resistance of about 150 pli or greater. Curing is initiated by a cure system, which includes a photoinitiator, as well as other optional components. Although exhibiting a high tear resistance, the inventive compositions also desirably provide a Shore A hardness of less than about 75, thereby providing soft, deformable compositions.

Urethane Acrylate Oligomers

The curable compositions of the present invention contain at least one urethane acrylate oligomer. The urethane acrylate oligomer may be selected from a variety of materials, most desirably aliphatic urethane acrylates. Useful urethane acrylates include di- or polyfunctionalized urethane acrylates, which are capable of cross-linking during cure.

Useful di- or polyfunctionalized urethane acrylates include aliphatic polyester urethane diacrylates. Such oligomers generally may be described as the reaction product of a polyester polyol and a polyisocyante. Aliphatic polyester urethane diacrylates having high molecular weights, such as 2,000 to 7,000, are particularly desirable. Other mono-, di-, or polyfunctional urethane acrylate oligomers useful in the present invention can be described as the acrylated reaction product of an aliphatic alcohol, such as polycarbonate polyol, a polyether polyol, or ethylene glycol monoacrylate, and a polyisocyanate.

Representative polyether polyols useful in preparing the urethane acrylate oligomers include straight or branched alkylene oxides having from one to twelve carbon atoms (C1-12), prepared by methods known in the art. Desirably the polyether polyols have an average molecular weight, as determined by vapor pressure osmometry (ASTM-D 3592), sufficient to give the urethane acrylate oligomer a molecular weight of about 6,000 daltons, desirably not more than 5,000 daltons and more desirably not more than 4,000 daltons. Examples include, without limitation, polytetramethylene polyol, polymethylene oxide polyol, polyethylene oxide polyol, polypropylene oxide polyol, polybutylene oxide polyol, tetrahydrofuran (THF)-sym-polyether polyol and combinations thereof.

Representative hydrocarbon polyols used to prepare the urethane-acrylate oligomers also include hydrocarbon polyols, straight or branched, having a molecular weight of from about 600 to 4,000. Non-limiting examples include fully or partially hydrogenated polybutadiene polyol, polybutadiene polyol hydrogenated to an iodine number of from 9 to 21, and fully or partially hydrogenated polyisobutylene polyol.

Representative polycarbonate polyols used to prepare the urethane-acrylate oligomers include but are not limited to the reaction products of dialkyl carbonate with an alkylene diol, optionally copolymerized with alkylene ether diols.

The polyisocyanates used to prepare the urethane-acrylate oligomers include aliphatics and aromatics having from 4 to 20 carbon atoms (C4-20). Representative aliphatic examples include isophorone diisocyanate, dicyclohexylmethane-4,4'-diisocyanate, 1,4-tetramethylene diisocyanate, 1,5-pentamethylene diisocyanate, 1,6-hexamethylene diisocyanate, 1,7-heptamethylene diisocyanate, 1,8-octamethylene diisocyanate, 1,9-nonamethylene diisocyanate, 1,10-decamethylene diisocyanate, 2,2,4-trimethyl-1,5-pentamethylene diisocyanate, 2,2'-dimethyl-1,5-pentamethylene diisocyanate, 3-methoxy-1,6-hexamethylene diisocyanate, 3-butoxy-1,6-hexamethylene, omega, omega'-dipropylether diisocyanate, 1,4-cyclohexyl diisocyanate, 1,3-cyclohexyl diisocyanate, trimethylhexylmethylene diisocyanate and combinations thereof.

Suitable catalysts for reacting the aliphatic alcohol with the polyisocyanate to form the urethane portion of the urethane-acrylate oligomers include such materials as: dibutyl tin dilaurate, dibutyl tin oxide, dibutyl tin di-2-hexoate, stannous oleate and octoate, lead octoate, ferrous acetoacetate; and amines, such as triethylamine, diethylmethylamine, triethylenediamine, dimethylethylamine, morpholine, N-ethyl morpholine, piperzine, N,N-dimethyl benzylamine, N,N-dimethyl laurylamine and combinations thereof.

The urethane oligomers thus formed are endcapped with a (meth)acrylate-containing group to form the tirethane-acrylate. Suitable hydroxyl-terminated endcapping monomers include, without limitation, hydroxyalkyl(meth)acrylates, such as hydroxyethyl (meth)acrylate, hydroxypropyl(meth)acrylate, hydroxybutyl(meth)acrylate, and the like. Combinations of endcapping groups may be employed.

The molar ratio of the polyol, polyisocyanate and endcapping monomer is desirably about 1:2:2, respectively.

A representative commercially available urethane acrylate oligomer useful in the compositions of the present invention is BOMAR BR-7432G (available from Bomar Specialties Co.). BOMAR BR-7432G is an aliphatic polyester urethane diacrylate having a high molecular weight. More particularly, the molecular weight of BOMAR BR-7432G is greater than about 4000. The viscosity of BOMAR BR-7432G (neat) is about 200,000 cps at 50° C. As formulated with 30% isobornyl acrylate (IBOA) and 2% IRGACURE 184, BOMAR BR-7432G exhibits the following properties: viscosity of about 72,000 in Pas at 25° C.; tensile strength of about 2880 psi; elongation percent of about 550; and Shore A hardness of about 84.

Another useful commercially available urethane acrylate oligomer is SARTOMER CN966J75 (available from Sartomer Company, Inc.). SARTOMER CN966J75 is an aliphatic polyester based urethane diacrylate oligomer blended with 25% IBOA. SARTOMER CN966J75 exhibits the following properties: viscosity of about 4,240 InPas at 60° C.; tensile strength of about 428 psi; and elongation percent of about 238.

In accordance with the present invention, the di- or polyfunctional urethane acrylate oligomers may be employed in amounts of about 30% to about 45% by weight of the total composition.

Reactive Diluents

The compositions of the present invention also contain at least one reactive diluent. Reactive diluents may be selected from those materials known in the art, and may be straight-chained, branched or cyclic, and may be at least partially aliphatic. The reactive diluent softens the urethane acrylate composition, for example, to exhibit a Shore A hardness of less than about 75 once cured, desirably ranging from about 60 to about 75 Shore A.

Desirable reactive diluents for use in the present invention are mono-functional monomers. A variety of mono-functional monomers may be used, such as, for example, isobornyl acrylate (IBOA). IBOA is a useful reactive diluent for oligomers.

Other useful reactive diluents include alkyl acrylates, methacrylates or alkoxylated alkyl(meth)acrylates, having about 6-18 carbon atoms in the alkyl moiety of the molecule. A useful example of an alkoxylated alkyl(meth)acrylate is 2(2-ethoxyethoxy)-ethyl acrylate (EOEOA), a slightly water dispersible mono-functional monomer.

Representative commercially available reactive diluents include SARTOMER SR-506 (IBOA) and SARTOMER SR-256 (2(2-ethoxyethoxy)-ethyl acrylate), from Sartomer Company, Inc., Exton, Pa.

Reactive diluents may be introduced independently in the overall composition or in a pre-mix of the urethane acrylate oligomer. In accordance with the present invention, reactive diluents may be employed in amounts sufficient to achieve the Shore A hardness values of about 60, which generally is in amounts of about 5% to about 75% by weight of the total composition. More desirably, embodiments of the present invention contain several reactive diluents, such as, for example, BOA in amounts of about 40% to about 50% and 2(2-ethoxyethoxy)-ethyl acrylate in amounts of about 5% to about 25% by weight of the total composition.

Cure System

In applications where deformable, soft hearing aid housings are to be made, the cure system is desirably one which is initiated by electromagnetic radiation. Photoradiation is desirable for its ability to produce a well-controlled cure and high quality parts efficiently. Various photoinitiators, such as UV, visible and infrared may be employed.

UV photoinitiators are generally effective in the 200 to 400 nm range, and particularly in the portion of the spectrum that borders on the invisible light and the visible portion just beyond this, e.g. >200 nm to about 390 nm.

A variety of UV photoinitiators may be employed. Photoinitiators, those that will respond to UV radiation to initiate and induce curing of the (meth)acryl functionalized curable component, which are useful in the present invention include benzophenone and substituted benzophenones, acetophenone and substituted acetophenones, benzoin and its alkyl esters, xanthone and substituted xanthoncs, diethoxy-acetophenone, benzoin methyl ether, benzoin ethyl ether, benzoin isopropyl ether, diethoxyxanthone, chloro-thio-xanthone, N-methyl diethanol-amine-benzophenone, 2-hydroxy-2-methyl-1-phenyl-propan-1-one, 2-benzyl-2-(dimethylamino)-1-[4-(4-morpholinyl)phenyl]-1-butanone and mixtures thereof. Photoinitiators suitable for use in the present invention that will respond to visible light to initiate and induce curing include camphoroquinone peroxyester initiators and 9-fluorene carboxylic acid peroxyesters. Thermal initiators include 2,2'-azobisisobutyronitrile. The initiators set forth above are for the purposes of illustration only and are in no way meant to limit the initiators that may be used in the present invention.

Examples of such UV initiators include photoinitiators available commercially from Ciba Specialty Chemicals Inc. under the "IRGACURE" and "DAROCUR" tradenames, specifically "IRGACURE" 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophonyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl)phosphine oxide and 2-hydroxy-2-methyl-1-phenyl-propan-1-one), and 819 [bis(2,4,6-trimethyl benzoyl) phenyl phosphine oxide], and "DAROCUR" 1173 (2-hydroxy-2-methyl-1-phenyl-1-propane) and 4265 (the combination of 2,4,6-trimethylbenzoyl-diphenyl-phosphine oxide and 2-hydroxy-2-methyl-1-phenyl-propan-1-one); the visible light [blue] photoinitiators, dl-camphorquinone and "IRGACURE" 784DC (photoinitiator based on substituted titanocenes); 2,4,6-trimethylbenzoyldiphenylphosphine oxide (commercially available as LUCIRIN TPO from BASF Corp.); and camphoroquinone/DMpT. Of course, combinations of these materials may also be employed herein.

Photoinitiators may be employed in amounts of about 0.5% to about 10% by weight of the total composition. More desirably, the photoinitiator is present in amounts of about 0.5% to about 5% by weight of the total composition.

The cure system also may include stabilizers and inhibitors, as well as chelating agents to control and prevent premature peroxide decomposition and polymerization. Among those useful inhibitors include phenols such as hydroquinone and quinones. Chelating agents may be used to remove trace amounts of metal contaminants. An example of a useful chelating agent is the tetrasodium salt of ethylenediamine tetraacetic acid (EDTA).

Optional Additives

A variety of optional additives also may be included in the compositions of the present invention. For instance, agents such as thickeners, plasticizers, fillers, elastomers, thermoplastics, dispersion stabilizers and other well-known additives may be incorporated where functionally desirable.

Various colorants also may be included in the inventive compositions. The term "colorants" is used to include dyes, pigments and other materials which can be used to impart color to the composition. Dyes are generally water-soluble organics, which often become water-insoluble once cured. Pigments may be organic or inorganic materials and are generally in the solid form. In particular, the compositions of the present invention are designed to work particularly well with the more dense solid pigments that are available. These pigments, due to their density and insolubility, tend to drop out of the dispersion and form a sediment in compositions to which they are added. The present invention is designed to overcome this sedimentation tendency, keep such dense insolubles in dispersion for a longer period of time and provide for color homogeneity to be re-established without substantial mixing.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobolt-alummina (turquoise), iron blue (blue), manganese (blue), chrome and chrome oxide (green) and titanium green; as well as black pigments, such as iron oxide black and carbon black.

Combinations of pigments are generally used to achieve the desired color tone in the cured composition. Titanium and iron oxides, in combination, are particularly useful in creating flesh tones for hearing aids, and tips.

The colorants may be present in the compositions of the present invention in amounts sufficient to render the desired color. Colorants may be present, for example, in amounts of about 0.1 to about 10.0%, desirably about 0.2 to about 2.0% and more desirably in amounts of about 0.2 to about 0.6% by weight of the total composition. Insoluble pigments are the desired form of colorant useful in the compositions of the present invention.

Tear Strength

Standard measurements of the tear strength of various substances are currently performed using tear resistance test procedures, such as those set forth in ASTM D1004 herein incorporated by reference. The tear resistance procedures are used for determining the initial tear resistance of plastic film and sheeting. These test methods measure the maximum force required to initiate tearing of a specimen.

Tear resistance measurements use a constant rate-of-grip separation machine, in which the test specimen is held between two grips (one fixed and one movable) in accordance with ASTM D1004. A drive member separates the two grips at a controlled velocity until complete rupture of the specimen, at which point the maximum tearing load and extension are recorded. From this data, the mean maximum resistance to tearing is calculated.

The curable compositions of the present invention, for example, may have a tear strength of at least about 75 pli (pounds per linear inch). In some embodiments, the tear strength may range from about 75 pli to about 250 pli, more desirably about 75 pli to about 150 pli.

Tensile Properties

Standard measurements of the tensile properties of various substances are currently performed using tensile test procedures, such as those set forth in ASTM D882 herein incorporated by reference. These tensile test procedures are used for determining tensile properties of plastics in the form of thin sheeting, including film. These test methods measure the force required to break a specimen and the extent to which the material stretches or elongates to that breaking point. A stress to strain diagram is produced from these tests, which is then used to determine tensile modulus.

Tensile property measurements use a constant rate-of-grip separation machine, in which the test specimen is held between two grips (one fixed and one movable) in accordance with ASTM D882. A drive member separates the two grips at a controlled velocity. The force required to elongate the test specimen is measured (with the corresponding amount of material that has elongated) until the specimen breaks. A stress-strain curve may be produced, from which modulus of elasticity is calculated. The modulus of elasticity is the ratio between the stress per unit area to the amount of deformation resulting from that stress. A high tensile modulus generally means that the material is more rigid, i.e., more stress is necessary to produce a given amount of strain.

The curable compositions of the present invention, for example, may have a tensile modulus of at least about 2,150 psi (pounds per square inch). Higher tensile modulus may be desired in embodiments having low hardness values in combination with high tear strength.

Hardness

Standard measurements of the hardness of various substances are currently performed using durometer hardness test procedures, such as those set forth in ASTM D2240 herein incorporated by reference. The durometer hardness procedures are used for determining indentation hardness of various substances, and are particularly useful for elastomeric materials. These test methods measure the depression force of a specific type of indentor as it is forced under specific conditions against the material's surface. Due to the various parameters which influence hardness determinations, different durometer scales have been established. A particular scale is chosen depending on the type of material to be measured. For example, materials which are relatively soft, such as elastomeric materials, are measured on a Shore A scale. Shore A scale measurements use a steel rod indenter shaped with a blunt end, and a calibrated spring force, as shown in FIG. 1 and Table 1, respectively of ASTM D2240. The indentor descends at a controlled rate against the specimen surface and a reading is recorded within a specified time period. This procedure is repeated multiple times at different positions on the specimen and the arithmetic mean of the results yields the Shore A measurement.

Durometer scales which are used for durometer hardness measurements include Shore A, B, C, D, DO, O, OO, and M. Each of theses scales has units from 0 to 100, There is no overlap between the scales, although certain materials may be suitable for testing on both scales. The geometry of the indenter and calibrated spring force scales influence the measurements, such that no simple relationship exists between the measurements obtained between different types of durometers. For example, the test for Shore D, which is designed for harder materials, is distinct from Shore A in that the indentor is shaped with a pointed tip and the calibrated spring force has a higher force scale then Shore A. Generally, this test is not suitable for materials which are measured on a Shore A scale.

The curable compositions of the present invention, for example, may have a Shore A hardness of less than about 75 once cured, desirably ranging from about 60 to about 75 Shore A.

Process of Making Hearing Aid Housing and Hearing Aid Assembly

The present invention also is directed to methods of making a hearing aid housing, as well as a hearing aid assembly, which includes a hearing aid housing mated to a soft tip component.

In accordance with the present invention, a method of making the hearing aid housing includes pouring the curable composition of the present invention into the mold cavity of a light-penetrable mold, the mold having an exposed, generally upward-facing surface. The composition covers a major amount of the generally upward-facing surface and fills the majority of the cavity. The surface is exposed to ultra-violet radiation through the transparent mold surface for a time and intensity sufficient to cure the composition. Desirably, the composition when cured produces a tear strength of at least about 75 pli, more desirably about 75 pli to about 250 pli, and a Shore A hardness ranging from about 60 to about 75.

The composition may be completely cured, or a portion may be cured to achieve a layer of cured composition having the shape of the cavity surface. The uncured composition above the cured material then may be poured off to leave the cured housing component. Depth of thickness of the housing may be controlled using a combination of UV initiators, light intensity and time. Additional cure of the housing, if necessary, also may be achieved by exposing the housing to additional photoradiation from the open end of the cavity once the uncured liquid is removed.

In accordance with some embodiments of the present invention, the hearing aid housing, prepared as described above, may be mated to a soft tip component to form a heating aid assembly. The soft tip component may be prepared in accordance with the curable composition and process described herein for making the hearing aid housing, or alternatively, the soft tip may be prepared in accordance with the disclosure of U.S. patent application Ser. No. 10/081,564, referred to above.

For instance, a method of making the soft tip may include pouring the curable composition disclosed in U.S. patent application Ser. No. 10/081,564 into the lower portion of a mold cavity, which is the tip cavity, of a light-penetrable mold, the mold having an exposed, generally upward-facing surface. The composition covers a major amount of the generally upward-facing surface of the tip cavity of the mold and fills the majority of the tip cavity. The surface is exposed to ultra-violet radiation through the transparent mold surface for a time and intensity sufficient to cure the composition to a Shore A hardness of about 55 or less.

Once the soft tip is cured, the curable composition of the present invention may be poured into the top section of the mold cavity, the housing cavity, and cured as described above in the process for making the hearing aid housing. The resulting material is a cured hearing aid housing, which is mated or adhered to the soft tip by crosslinkage.

The present invention also contemplates additional methods of making a hearing aid housing and/or assembly, which employ solid freeform fabrication techniques, particularly stereolithography and Inkjet processes. Stereolithography uses an additive, built-up process to form a three-dimensional article, which is commonly referred to as rapid prototyping. In particular, stereolithography uses photo-radiation to cure additive layers of a composition to form a polymeric article, e.g., a hearing aid housing.

As described in U.S. Pat. No. 6,540,045, which is incorporated herein by reference, stereolithography uses data of the three-dimensional shape of the area of application in an individual's ear to control the layer by layer process of forming the article. In accordance with such a process, a first layer of the article, e.g. hearing aid housing, is solidified (cured) at the surface of the curable composition by photo-radiation. A UV laser may be used for curing. Desirably, the first layer corresponds to a cross-sectional area of the article being formed, i.e., the area of application in the individual's ear. This may be achieved by controlling the UV laser with the digitized three-dimensional data of the area of application. The first cured layer then is covered by a new layer of the curable composition, which is solidified by photo-radiation. Layers are repeatedly added and solidified in this manner until the article having the desired shape is formed.

Stereolithography techniques also are described in detail in U.S. Pat. Nos. 6,533,062, 6,413,697, and 6,136,497, each of which is incorporated herein by reference.

In accordance with the various methods of the present invention, the resulting hearing aid housings are self-supporting, free from surface blemishes and uniform in color. They can be pigmented to match a variety of skin tones and are ideally suited for hearing aid components.

The following examples are intended to be non-limiting illustrations of compositions of the present invention.

EXAMPLES

A curable composition was prepared in accordance with the present invention and tested for various physical properties. Table 1 below lists the weight percent ranges for each component contained in the inventive curable composition. Once cured, the composition was tested for: stress at break (determined in accordance with ASTM D-882); strain at break (determined in accordance with ASTM D-882); modulus (determined in accordance with ASTM D-882); tear strength (determined in accordance with ASTM D-1004); and hardness (determined in accordance with ASTM D-2240).

TABLE 1

| COMPONENT | WEIGHT % |
| --- | --- |
| High molecular weight aliphatic polyester urethane diacrylate[1] | 30-45 |
| IBOA | 40-50 |
| EOEOEA | 10-20 |
| Photoinitiator | 0.5-5 |

[1]BOMAR BR-7432G (Bomar Specialties Co.)

A comparative curable composition was prepared in accordance with application Ser. No. 10/081,564, referred to above. Table 2 below lists the weight percents for each component included in the comparative composition.

TABLE 2

| COMPONENT | WEIGHT % |
| --- | --- |
| Aliphatic urethane diacrylate[1] | 29.10 |
| Aliphatic urethane diacrylate[2] | 14.10 |
| IBOA | 26.90 |
| EOEOEA | 9.00 |
| Monofunctional urethane acrylate oligomer[3] | 15.90 |
| Photoinitiator[4] | 5.00 |

[1]Sartomer CN-966J75 (Sartomer Co.)
[2]MegaFlex (Loctite)
[3]Genomer 1122 (Hans Rahn & Co.)
[4]Sartomer KIP-100 (Sartomer Co.)

After curing, the comparative composition (Table 2) was subjected to the same physical property tests as the inventive composition (Table 1). The comparative data for the two compositions with respect to each property is provided in Table 3 below.

TABLE 3

| PHYSICAL PROPERTY | INVENTIVE COMPOSITION | COMPARATIVE COMPOSITION |
| --- | --- | --- |
| Stress at break (psi) | 1,340 | 1,350 |
| Strain at break (%) | 210 | 350 |
| Modulus (psi) | 2,150 | 175 |
| Tear strength (pli) | 150 | 25 |
| Hardness (Shore A) | 60 | 47 |

As evidenced by the data in Table 3, the inventive compositions have a higher tear strength and tensile modulus than the softer comparative compositions. The Shore A value of the inventive composition is 60, whereas the comparative composition has a lower Shore A value of 47. Although harder than the comparative compositions, however, the inventive compositions are still sufficiently soft to be deformable with a Shore A hardness of about 60. Moreover, the inventive compositions exhibit a substantially higher resistance to tearing (e.g., 150 pli vs. 25 pli) and a higher modulus (2,150 psi vs. 175 psi), and thereby produce tougher components. Accordingly, the inventive compositions are useful for hearing aid applications, particularly hearing aid housings. The compositions are soft and deformable, which increases overall comfort in the ear, yet highly tear resistant and durable, which permits removal and replacement of outer housings without damaging electronic components of the hearing aid assembly.

What is claimed is:

1. A hearing aid housing comprising the reaction product of a curable composition of:
    (a) at least one urethane acrylate oligomer comprising an aliphatic polyester urethane diacrylate present in amounts of about 30% to about 45% by weight of said composition;
    (b) at least one reactive diluent comprising isobornyl acrylate present in amounts of about 40% to about 50% by weight of said composition;
    (c) 2(2-ethoxyethoxy) ethyl acrylate present in amounts of about 5% to about 25% by weight of said composition; and
    (d) a photoinitiator present in amounts of about 0.5% to about 10% by weight of said composition;
wherein said composition when cured produces a tear strength of at least about 75 pli.

2. A method of making a hearing aid housing comprising the steps of:
    (a) combining a curable composition comprising:
        (i) at least one urethane acrylate oligomer;
        (ii) at least one reactive diluent; and
        (iii) a cure system;
    (b) pouring the curable composition into a mold cavity of a mold;
    (c) exposing the composition to photo-radiation for a time and intensity sufficient to fully cure the composition to produce a tear strength of at least 75 pli;
    (d) combining a soft tip composition comprising:
        (i) a urethane acrylate oligomer comprising at least one di-functional urethane acrylate and at least one mono-functional urethane acrylate;
        (ii) a reactive diluent; and
        (iii) a cure system;
    (e) pouring the soft tip composition into a mold cavity of a mold;
    (f) exposing the composition to photo-radiation for a time and intensity sufficient to fully cure the composition to produce a soft tip having a Shore A hardness of about 55 or less; and
    (g) mating the soft tip to the hearing aid housing.

3. A method of making a hearing aid housing comprising the steps of:
    (a) providing data of the three-dimensional shape of an area in an individual's ear for application of a hearing aid housing;
    (b) combining a curable composition comprising:
        (i) at least one urethane acrylate oligomer comprising an aliphatic polyester urethane diacrylate present in amounts of about 30% to about 45% by weight of said composition;
        (ii) at least one reactive diluent comprising isobornyl acrylate present in amounts of about 40% to about 50% by weight of said composition;
        (iii) 2(2-ethoxyethoxy) ethyl acrylate present in amounts of about 5% to about 25% by weight of said composition; and
        (iv) a cure system comprising a photoinitiator present in amounts of about 0.5% to about 10% by weight of said composition;
    (c) exposing the composition to photo-radiation for a time and intensity sufficient to cure a layer on the surface of the composition which corresponds to a cross-section of the three-dimensional area in the individual's ear;
    (d) covering the cured layer with a new layer of the composition and exposing the new layer to photo-radiation for a time and intensity sufficient to cure the new layer; and
    (e) repeating step (c) until the hearing aid housing is formed.

4. The method of claim 3, wherein each layer of the curable composition is cured to produce a tear strength of at least about 75 pli.

5. The method of claim 3, wherein the step of exposing the composition to photo-radiation comprises exposing the composition to a UV laser which is controlled by the three-dimensional data of the area in the individual's ear.

6. The hearing aid housing of claim 1, wherein the reaction product produces one or more properties selected from the group consisting of: tear strength of at least about 75 pli; Shore A hardness of about 60 to about 75; and tensile modulus of at least about 2,150 psi.

7. The hearing aid housing of claim 1, wherein the urethane acrylate oligomer has a molecular weight of about 2,000 to about 7,000.

* * * * *